United States Patent [19]

Wakselman et al.

[11] 4,246,200
[45] Jan. 20, 1981

[54] PERFLUORO INTERMEDIATES AND PROCESSES FOR THEIR PREPARATION

[75] Inventors: Claude Wakselman, Villebon; Marc Tordeux, Fontenay-aux-Roses, both of France

[73] Assignee: Agence Nationale de Valorisation de la Recherche (ANVAR), Neuilly-sur-Seine, France

[21] Appl. No.: 43,042

[22] Filed: May 29, 1979

[30] Foreign Application Priority Data

Jun. 8, 1978 [FR] France .................................. 78 17163

[51] Int. Cl.³ .......................................... C07C 119/00
[52] U.S. Cl. .................................. 564/248; 562/605; 568/271; 568/278; 568/1; 568/384; 564/442; 564/453; 564/462; 564/510
[58] Field of Search ..................................... 260/566 D

[56] References Cited

U.S. PATENT DOCUMENTS

| 3,325,543 | 6/1967 | Degener et al. | 260/566 D |
| 3,541,091 | 11/1970 | Zecher et al. | 260/566 D |
| 3,847,988 | 11/1974 | Gold | 260/566 D |

FOREIGN PATENT DOCUMENTS

| 1154089 | 9/1963 | Fed. Rep. of Germany | 260/566 D |
| 696504 | 9/1953 | United Kingdom | 260/566 D |

*Primary Examiner*—James H. Reamer
*Attorney, Agent, or Firm*—Young & Thompson

[57] ABSTRACT

This invention relates to compounds having the formula

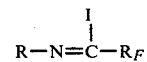

in which $R_F$ is a perfluoro radical $C_nF_{2n+1}$ with $n = 1$–20, and R is a $C_{1-20}$ alkyl radical, a $C_{4-15}$ cycloalkyl radical, a $C_{5-20}$ cycloalkyl-alkyl radical, or a $C_{6-20}$ aromatic radical.

Said compounds constitute valuable intermediates for the synthesis of surface-active agents.

7 Claims, No Drawings

PERFLUORO INTERMEDIATES AND PROCESSES FOR THEIR PREPARATION

This invention relates to the synthesis of perfluoro derivatives and, more particularly, the synthesis of perfluoro acids and their derivatives.

The derivatives of perfluoro acids of the formula $R_FCOOH$ in which $R_F$ is a perfluoro radical $C_nF_{2n+1}$ (n=1-20), and typically their salts, are useful surfactants in view of the hydrophobic properties of the perfluoroalkyl chains (see M. C. Allison & P. J. Weber Informations Chimie May 1978 No. 177 p.117).

Said acids are generally obtained by electrolysis in hydrofluoric acid (M. HUDLICKY "Chemistry of organic fluorine compounds" 2nd Edition, John Wiley N.Y. 1976, p.73) or by carbonatation of organometallic derivatives prepared from perfluoroalkyl iodides $R_FI$ (loc.cit., p.372; H. BLANCOU, P. MOREAU & A. COMMEYRAS, J. Chem. Soc. Chem. Comm., 1976, 885 and references mentioned). Such acids are converted to salts, esters, amides and other derivatives according to usual methods.

The object of this invention is to provide a simpler route for the synthesis of such compounds.

Thus, this invention relates to new perfluoro compounds which provide ready access to perfluoro acids and their derivatives, and also to a simple process for the preparation of said new perfluoro compounds.

The new perfluoro compounds of this invention are perfluoro imidoyl iodides having the formula (I):

$$R-N=C-R_F \quad \text{(I)}$$
with I above C in which $R_F$ is a perfluoro radical $C_nF_{2n+1}$ in which n=1-20, and R is a $C_{1-20}$ alkyl radical, a $C_{4-15}$ cycloalkyl radical, a $C_{5-20}$ cycloalkyl-alkyl radical or a $C_{6-20}$ aromatic radical.

According to the present invention, the perfluoro imidoyl iodides of the formula (I) are prepared by addition of a perfluoroalkyl iodide $R_FI$ to an isonitrile of the formula $R-N\equiv C$.

This addition may be effected by simply mixing the reagents in the presence of copper or silver metal. The reaction is preferably effected in the presence of copper powder. The reaction may be effected in the absence or in the presence of a solvent such as acetonitrile, ethyl ether, benzene or hexane. The exothermal reaction occurs generally at room temperature. In some cases, to speed up the reaction, it is convenient to heat the reaction mixture, at the reflux temperature of the solvent, for example.

The reaction is advantageously effected with at least a stoichiometric amount of isonitrile $R-N\equiv C$, preferably with 1-2 moles isonitrile per mole perfluoroalkyl iodide $R_FI$.

As a modification, the compounds of the formula (I) in which R is other than a tert.alkyl radical or an aromatic radical may be obtained by heating within an inert solvent. Typical useful solvents include benzene, toluene and heptane. The reaction is advantageously effected at the reflux temperature of the solvent. The reaction is preferably effected in the presence of a free-radical initiator, typically azobisisobutyronitrile or a peroxide such as benzoyl peroxide. The reaction is advantageously effected with stoichiometric amounts of the reagents.

In contrast, it is to be noted that no such addition is found to occur when it is attempted to react an alkyl iodide such as methyl iodide with an isonitrile under the same reaction conditions.

The starting isonitriles are now readily available due to new methods for the dehydration of formamides (U. SCHOLLKOPF, Angew. Chem. Int., 1977, 16, 339; G. SKORNA & UGI, Angew. Chem. Int. Ed. 1977, 16, 259) or to the use of phase-transfer agents for the Hofmann reaction (U. SCHOLLKOPF, Angew. Chem. Int. Ed. 1977, 16, 339). In addition, in contrast to the organometallic route, the process of this invention does not require a highly anhydrous solvent and is applicable to substantial amounts of raw materials.

The perfluoro imidoyl iodides of the formula (I) constitute valuable synthesis intermediates. Indeed, they provide a ready route to the production of a large number of perfluoro compounds, and particularly to perfluoro compounds useful as surface active agents.

Thus, hydrolysis with a strong base in alcohol medium gives the acid of the formula $R_FCOOH$. It may be preferable, however, first to effect a hydrolysis with an acid under refluxing conditions, to give an amide of the formula $R_FCONHR$ which is then saponified with a strong base in alcohol medium, at room temperature. In addition, reduction of the compounds of the formula (I), typically with $BH_4$, gives amines of the formula $R_FCH_2NHR$.

The following non-limiting Examples illustrate the present invention. In the Examples, the IR spectra are recorded in $CCl_4$, and the NMR spectra at 56.4 MHz in $CDCl_3$ with $CFCl_3$ as internal standard (the chemical shift of the signals of the $CF_2$ α to the functional group is given).

EXAMPLE 1

Preparation of $C_6F_{13}CINC_6H_{11}$

To 0.1 mole $C_6F_{13}I$ is added 0.117 mole cyclohexyl isocyanide. After homogenization, 0.01 g-at. copper powder is added thereto. The mixture is stirred for 10 seconds and is then allowed to stand. After a few minutes, an exothermal reaction is found to occur. The reaction mixture is left standing for 2 hours, after which the copper is filtered off and the product is distilled under high vacuum.

Yield: 87% (with respect to $C_6F_{13}I$). B.p.=70° C./0.1 mm Hg
IR: 1685 cm$^{-1}$. NMR: 109 ppm.

EXAMPLE 2

Preparation of $C_6F_{13}CIN$ nBu

The procedure of Example 1 is used, using 0.131 mole n-butyl isocyanide.
Yield: 90%. B.p.=60° C./0.5 mm Hg.
IR: 1690 cm$^{-1}$. NMR: 109 ppm.

EXAMPLE 3

Preparation of $C_6F_{13}CIN$ nBu

The procedure of Example 1 is used, using 0.153 mole t-butyl isocyanide.
Yield: 70%. B.p.=61° C./0.8 mm Hg.
IR: 1703 cm$^{-1}$. NMR: 108 ppm.

EXAMPLE 4

Preparation of $C_6F_{13}CIN\ CH_2C_6H_5$

The procedure of Example 1 is used, using 0.2 mole benzyl isocyanide. Ethyl ether is added prior to the filtration step. A Cu-isonitrile complex precipitate is also separated. After filtration, the ether is evaporated off.

Yield: 32%. B.p.=92° C./0.2 mm Hg.
IR: 1680 cm$^{-1}$. NMR: 109 ppm.

EXAMPLE 5

Preparation of

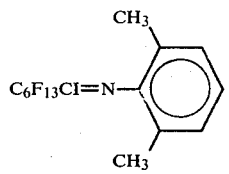

To 13.5 g $C_6F_{13}I$ are added 3.93 g 2,6-dimethyl-phenyl isocyanide in 10 ml benzene with 0.18 g Cu. The reaction is heated to the refluxing temperature of benzene for 3 hours, and is then filtered. After evaporation of the benzene, the product is rapidly distilled in vacuo and is then sublimed at 60° C./0.5 mm.

Yield: 52%. M.p.=45° C.
IR: 1680 cm$^{-1}$. NMR: 109 ppm.

EXAMPLE 6

Preparation of $C_6F_{13}CIN\ nBu$ (modification)

A mixture of 18 g $C_6F_{13}I$ and 3.3 g butyl isocyanide in 10 ml benzene and 0.2 g azobisisobutyronitrile is refluxed for 24 hours. The benzene is evaporated off and the product is distilled in vacuo.

Yield: 80%. B.p.=60° C./0.5 mm Hg.
IR: 1685 cm$^{-1}$. NMR 109 ppm.

EXAMPLES 7–11

The procedure of Example 6 is used, with the isocyanides and perfluoroalkyl iodides tabulated in Table I. The yields and the characteristics of the compounds of the formula (I) are given in the Table.

TABLE I

| Ex. | $R_F$ | R | Yield % | B.p. °C./ mm Hg | IR | NMR $^{19}F$ |
|---|---|---|---|---|---|---|
| 7 | $C_4F_9$ | n-butyl | 64 | 82/23 | 1695 | 109 |
| 8 | $C_4F_9$ | cyclohexyl | 61 | 102/23 | 1690 | 110 |
| 9 | $C_6F_{13}$ | cyclohexyl | 61 | 70/0.1 | 1685 | 109 |
| 10 | $C_8F_{17}$ | n-butyl | 72 | 72/0.5 | 1685 | 109 |
| 11 | $C_8F_{17}$ | cyclohexyl | 80 | 107/0.3 | 1685 | 110 |

EXAMPLE 12

Preparation of perfluoro amine $C_6F_{13}\ CH_2NHBu$

To 5.3 g $C_6F_{13}CINBu$ in 10 cc absolute ethanol is added 0.38 g $NaBH_4$, with stirring. The reaction mixture is stirred for 2 hrs, after which 4 g $C_6H_{13}CH_2NHBu$ are distilled.

Yield: 90%. B.p.=70° C./15 mm Hg. RMN: 122.7 ppm.

EXAMPLE 13

Preparation of perfluoro amine $C_8F_{17}CONHBu$ 0.01 mole $C_8F_{17}CINBu$ (6.3 g) is refluxed in 10 cc 20% sulfuric acid for 12 hours. After extraction with ether and washing with a sodium thiosulfate solution, the amide is sublimed in vacuo (60° C./0.3 mm Hg).

Yield: 82%. M.p.=58°–60° C. IR 1730 cm$^{-1}$. NMR 127 ppm.

EXAMPLES 14–16

The procedure of Example 13 is used, from the imidoyl iodides tabulated in Table II.

The yields and the characteristics of the amides of the formula $R_FCOHNR$ are given in Table II.

TABLE II

| Ex. | $R_F$ | R | Yield % | B.p. °C./ mm Hg | M.P. °C. | IR | NMR $^{16}F$ |
|---|---|---|---|---|---|---|---|
| 14 | $C_4F_9$ | n-butyl | 81 | 68/0.3 | — | 3460 1730 | 125 |
| 15 | $C_6F_{13}$ | cyclo-hexyl | 77 | — | 68 | 3440 1725 | 125 |
| 16 | $C_8F_{17}$ | cyclo-hexyl | 71 | — | 76 | 3435 1735 | 127 |

EXAMPLE 17

Preparation of perfluoro acid $C_8F_{17}COOH$ 15 g $C_8F_{17}$ CONHBu in 20 ml 2 N alcoholic sodium hydroxide are stirred for 4 hours. The material is made acidic with 2 N hydrochloric acid and extracted 6 times with ether. 8 g $C_8F_{17}COOH$ are dried at 50° C./20 mm Hg.

Yield: 66%. IR 1750 cm$^{-1}$.
NMR 124 ppm.

Having now described our invention what we claim as new and desired to secure by Letters Patent is:

1. A compound having the formula:

in which $R_F$ is a perfluoro group $C_nF_{2n+1}$ with n=1–20, and R is selected from $C_{1-20}$ alkyl, $C_{4-15}$ cycloalkyl, $C_{5-20}$ cycloalkyl-alkyl, benzyl and 2,6-dimethyl phenyl.

2. Process for the preparation of a compound having the formula:

in which $R_F$ is perfluoro group $C_nF_{2n+1}$ with n=1–20, R is selected from $C_{1-20}$ alkyl other than tert. alkyl, $C_{4-15}$ cycloalkyl and $C_{5-20}$ cycloalkyl-alkyl, comprising reacting a perfluoroalkyl iodide having the formula $R_FI$ with an isonitrile having the formula $RN\equiv C$, by heating in an inert solvent, in which formulae $R_F$ and R have the meanings given above.

3. Process for the preparation of a compound having the formula:

in which $R_F$ is perfluoro group $C_nF_{2n+1}$ with n=1-20, and R is selected from $C_{1-20}$ alkyl, $C_{4-15}$ cycloalkyl, $C_{5-20}$ cycloalkyl-alkyl, benzyl and 2,6-dimethyl phenyl, comprising reacting a perfluoroalkyl iodide having the formula $R_FI$ with an isonitrile having the formula $RN=C$, in which formulae $R_F$ and R have the meanings given above, in the presence of copper or silver metal.

4. Process as claimed in claim 3, wherein the reaction is effected with 1-2 moles isonitrile per mole perfluoroalkyl iodide.

5. Process as claimed in claim 2, wherein the reaction is effected at the reflux temperature of the solvent.

6. Process as claimed in claim 2 or 5, wherein the reaction is effected in the presence of a free-radical initiator.

7. Process as claimed in any one of claims 2, 5 or 6, wherein the reaction is effected with stoichiometric amounts of the reagents.

* * * * *